United States Patent
Sueda et al.

(10) Patent No.: US 9,376,319 B2
(45) Date of Patent: Jun. 28, 2016

(54) ROUNDED ZINC PEROXIDE PARTICLES, ROUNDED ZINC OXIDE PARTICLES, METHOD FOR PRODUCTION THEREOF, COSMETIC AND HEAT RELEASING FILLER

(75) Inventors: Satoru Sueda, Iwaki (JP); Atsuki Terabe, Iwaki (JP); Mitsuo Hashimoto, Iwaki (JP); Koichiro Magara, Iwaki (JP); Keita Kobayashi, Sakai (JP)

(73) Assignee: Sakai Chemical Industry Co., Ltd., Osaka (JP)

( * ) Notice: Subject to any disclaimer, the term of this patent is extended or adjusted under 35 U.S.C. 154(b) by 57 days.

(21) Appl. No.: 14/123,874

(22) PCT Filed: Jun. 8, 2012

(86) PCT No.: PCT/JP2012/064777
§ 371 (c)(1),
(2), (4) Date: Feb. 5, 2014

(87) PCT Pub. No.: WO2012/169611
PCT Pub. Date: Dec. 13, 2012

(65) Prior Publication Data
US 2014/0212669 A1    Jul. 31, 2014

(30) Foreign Application Priority Data
Jun. 10, 2011 (JP) .................................. 2011-130580

(51) Int. Cl.
C01G 9/02    (2006.01)
B32B 5/16    (2006.01)
C01B 15/047  (2006.01)
C09C 1/04    (2006.01)
C09K 5/14    (2006.01)
(Continued)

(52) U.S. Cl.
CPC .............. *C01B 15/047* (2013.01); *A61K 8/0241* (2013.01); *A61K 8/27* (2013.01);
(Continued)

(58) Field of Classification Search
CPC ................. C01B 15/04; C01B 15/047; C08K 2003/2296; C01G 9/02
USPC .................... 423/272, 582, 622, 101; 428/402
See application file for complete search history.

(56) References Cited

U.S. PATENT DOCUMENTS 2,304,098 A * 12/1942 Jones et al. ................... 424/614
4,394,488 A *  7/1983 Kim et al. ..................... 524/432
(Continued)

FOREIGN PATENT DOCUMENTS

CN      101152957 A      4/2008
JP      01-290509 A   * 11/1989
(Continued)

OTHER PUBLICATIONS

Uekawa et al., Nonstoichiometric properties of zinc oxide nanoparticles prepared by decomposition of zinc peroxide, Phys. Chem. Chem. Phys., 2—3, 5, 929-934.*
(Continued)

*Primary Examiner* — Holly Le
(74) *Attorney, Agent, or Firm* — Polsinelli PC

(57) ABSTRACT

An object of the present invention is to provide rounded zinc peroxide particles having a large particle diameter, the rounded zinc peroxide particles having excellent performance because they have an average particle diameter of 0.04 μm or more, a small aspect ratio and a shape close to a spherical shape; rounded zinc oxide particles which are obtained by calcinating the rounded zinc peroxide particles and which have a small aspect ratio and a sharp particle size distribution; a method for production thereof; and a cosmetic and a heat releasing filler each containing the rounded zinc oxide particles. Provided are rounded zinc peroxide particles having an average particle diameter of 0.04 μm or more and an aspect ratio of 2.0 or less, and rounded zinc oxide particles which are obtained by thermally decomposing the rounded zinc peroxide particles and which have an average particle diameter of 0.04 μm or more and an aspect ratio of 2.0 or less.

1 Claim, 8 Drawing Sheets

(51) Int. Cl.
  *A61K 8/27* (2006.01)
  *A61Q 17/04* (2006.01)
  *A61Q 19/00* (2006.01)
  *A61K 8/02* (2006.01)
  *B82Y 30/00* (2011.01)
  *C01G 9/00* (2006.01)

(52) U.S. Cl.
  CPC .............. *A61Q 17/04* (2013.01); *A61Q 19/00* (2013.01); *B82Y 30/00* (2013.01); *C01G 9/02* (2013.01); *C09C 1/04* (2013.01); *C09C 1/043* (2013.01); *C09K 5/14* (2013.01); *A61K 2800/412* (2013.01); *C01G 9/00* (2013.01); *C01P 2002/72* (2013.01); *C01P 2004/32* (2013.01); *C01P 2004/51* (2013.01); *C01P 2004/54* (2013.01); *C01P 2004/64* (2013.01); *C01P 2006/12* (2013.01); *C01P 2006/60* (2013.01); *Y10T 428/2982* (2015.01)

(56) References Cited

U.S. PATENT DOCUMENTS

| 4,427,644 | A | 1/1984 | Doetsch et al. |
| 5,093,099 | A | 3/1992 | Haishi et al. |
| 7,423,512 | B1 | 9/2008 | Reitz et al. |
| 2011/0081548 | A1 | 4/2011 | Sueda et al. |
| 2011/0081550 | A1 | 4/2011 | Sueda et al. |

FOREIGN PATENT DOCUMENTS

| JP | H01-290509 A | 11/1989 |
| JP | H03-183620 A | 8/1991 |
| JP | H07-25614 A | 1/1995 |
| JP | H11-302015 A | 11/1999 |
| JP | 2002194379 A | 7/2002 |
| JP | 2003-026422 A | 1/2003 |
| JP | 2007-084354 A | 4/2007 |
| JP | 2009249226 A | 10/2009 |

OTHER PUBLICATIONS

Singh et al., Controlling the flow of nascent oxygen using hydrogen peroxide results in controling the synthesis of ZnO/ZnO2, Chalcogenide Lett., vol. 7, No. 4, 2010, 275-281.*

WHC International Co. Ltd brochure, Zinc oxide, 2006.*

Uekawa et al., "Synthesis of ZnO Nanoparticles by Decomposition of Zinc Peroxide", The Chemical Society of Japan, Chemistry Letters 2001; pp. 606-607.

\* cited by examiner

ROUNDED ZINC PEROXIDE PARTICLES, ROUNDED ZINC OXIDE PARTICLES, METHOD FOR PRODUCTION THEREOF, COSMETIC AND HEAT RELEASING FILLER

CROSS REFERENCE TO RELATED APPLICATIONS

This application is a National Phase filing under 35 U.S.C. §371 of PCT/JP2012/064777 filed on Jun. 8, 2012; and this application claims priority to Application No. 2011-130580 filed in Japan on Jun. 10, 2011; the entire contents of all are hereby incorporated by reference.

TECHNICAL FIELD

The present invention relates to rounded zinc peroxide particles, rounded zinc oxide particles, a method for production thereof, a cosmetic and a heat releasing filler.

BACKGROUND OF THE DISCLOSURE

Zinc peroxide is used as a cross-linker of a carboxyl group in production of a nitrile rubber, a deodorant, a bactericide, a bleaching agent, a curing agent, a photocatalyst and the like. Zinc peroxide may be added to fireworks etc. as an oxidant. Further, zinc peroxide turns to zinc oxide when calcinated, and therefore can also be used as an intermediate material for production of zinc oxide. As a method for production of such zinc peroxide particles, Patent Document 1 describes a method in which a precipitate of zinc hydroxide obtained by adding a basic solution to a solution containing a zinc salt is dispersed in hydrogen peroxide water, and the dispersion is subjected to a heating treatment to obtain a fine particle dispersion sol of zinc oxide.

In the production method, however, fine zinc peroxide particles having a high specific surface area are produced, and round-shaped zinc peroxide particles having an average particle diameter of 0.04 µm or more cannot be obtained. Fine zinc peroxide particles having a small particle diameter have the problem that it is difficult to form zinc oxide particles while maintaining the shape/size of zinc peroxide particles because finer particles have a stronger cohesive force, so that fusion of particles more easily proceeds when zinc oxide particles are formed by thermal decomposition. For rectifying the above-mentioned problem, zinc peroxide particles having a larger particle diameter are desired. However, such zinc peroxide particles having a large particle diameter and a method for production thereof are unknown. For arbitrarily controlling the reactivity of zinc peroxide, such as oxidizing power and photocatalytic activity, for example, a method is conceivable in which by controlling the particle diameter, the surface area of particles is controlled to control the reactivity of zinc peroxide. However, a method for controlling the particle diameter of zinc peroxide particles with high accuracy in a particle diameter region of 0.04 µm or more is unknown.

Further, zinc oxide particles are used in many applications such as ultraviolet blocking agents in cosmetics and heat releasing fillers. In these applications, fine zinc oxide particles having a particle diameter of 0.1 µm or less (for example, Patent Documents 2 and 3), and zinc oxide particles having a particle diameter of more than 1.0 µm are largely examined, but round-shaped zinc oxide particles having a particle diameter of about 0.04 to 1.0 µm are not so much examined, and a method for production thereof is not fully established. Recently, however, zinc oxide particles having the above-mentioned particle diameters have been becoming required for applications such as cosmetics and heat releasing fillers from the viewpoint of improvement of ultraviolet blocking performance, improvement of visible light transparency, use in heat releasing fillers of particles having such an intermediate size as to increase the filling rate when the particles are used in combination with a heat releasing filler having a large particle diameter, and so on.

These rounded zinc oxide particles having a particle diameter of 0.04 to 1.0 µm have a small aspect ratio and a shape close to a spherical shape, and therefore when they are used as a heat releasing filler in combination with particles having a large particle diameter for the purpose of enhancing thermal conduction, thermal conduction can be enhanced more efficiently than when zinc oxide particles, which have a similar particle size but do not have a rounded shape, are compounded.

PRIOR TECHNICAL DOCUMENTS

Patent Documents

[Patent Document 1] Japanese Kokai Publication 2003-26422
[Patent Document 2] Japanese Kokai Publication Hei11-302015
[Patent Document 3] Japanese Kokai Publication Hei3-183620

SUMMARY OF INVENTION

Problems to be Solved by the Invention

In the situations described above, an object of the present invention is to provide rounded zinc peroxide particles having a particle diameter larger than that of conventional zinc peroxide particles, the rounded zinc peroxide particles having excellent performance because they have an average particle diameter of 0.04 µm or more, a small aspect ratio, i.e. 2.0 or less and a rounded shape close to a spherical shape; rounded zinc oxide particles obtained by calcinating the rounded zinc peroxide particles; a method for production thereof; a cosmetic containing the rounded zinc oxide particles; and a heat releasing filler comprising the rounded zinc oxide particles.

Means for Solving Object

The present invention provides rounded zinc peroxide particles having an average particle diameter of 0.04 µm or more and an aspect ratio of 2.0 or less.

The rounded zinc peroxide particles are preferably those obtained by a step (1) of treating zinc oxide particles with hydrogen peroxide.

The present invention also provides rounded zinc oxide particles which are obtained by thermally decomposing the rounded zinc peroxide particles and which have an average particle diameter of 0.04 µm or more and an aspect ratio of 2.0 or less.

The rounded zinc oxide particles preferably have a D90/D10 of 3.0 or less in particle size distribution.

The rounded zinc oxide particles preferably have a specific surface area of 30 m$^2$/g or less.

The present invention also provides a method for production of the rounded zinc peroxide particles described above, the method comprising a step (1) of treating zinc oxide particles with hydrogen peroxide.

The present invention also provides a method for production of the rounded zinc oxide particles described above, the method comprising a step (1) of treating zinc oxide particles with hydrogen peroxide and a step (2) of calcinating and thereby thermally decomposing the rounded zinc peroxide particles obtained in the step (1).

The present invention also provides a cosmetic containing the rounded zinc oxide particles described above.

The present invention also provides a heat releasing filler comprising the rounded zinc oxide particles described above.

Effects of the Invention

Since the rounded zinc peroxide particles of the present invention have a large particle diameter, i.e. an average particle diameter of 0.04 μm or more, a small aspect ratio, i.e. 2.0 or less, and a rounded shape close to a spherical shape, and the reactivity of zinc peroxide is appropriately controlled, the rounded zinc peroxide particles have excellent effects in various kinds of applications.

The rounded zinc oxide particles of the present invention have excellent ultraviolet blocking performance and also excellent transparency, and therefore can be suitably used as an ultraviolet blocking agent for cosmetics. Further, the rounded zinc oxide particles also have the advantage that they are excellent in uniformity in the particle diameters and shape. When the rounded zinc oxide particles are used as a heat releasing filler, they exhibit excellent heat releasing performance particularly when used in combination with other heat releasing fillers having a large particle diameter.

DETAILED DESCRIPTION OF PREFERRED EMBODIMENTS

Figure 1:
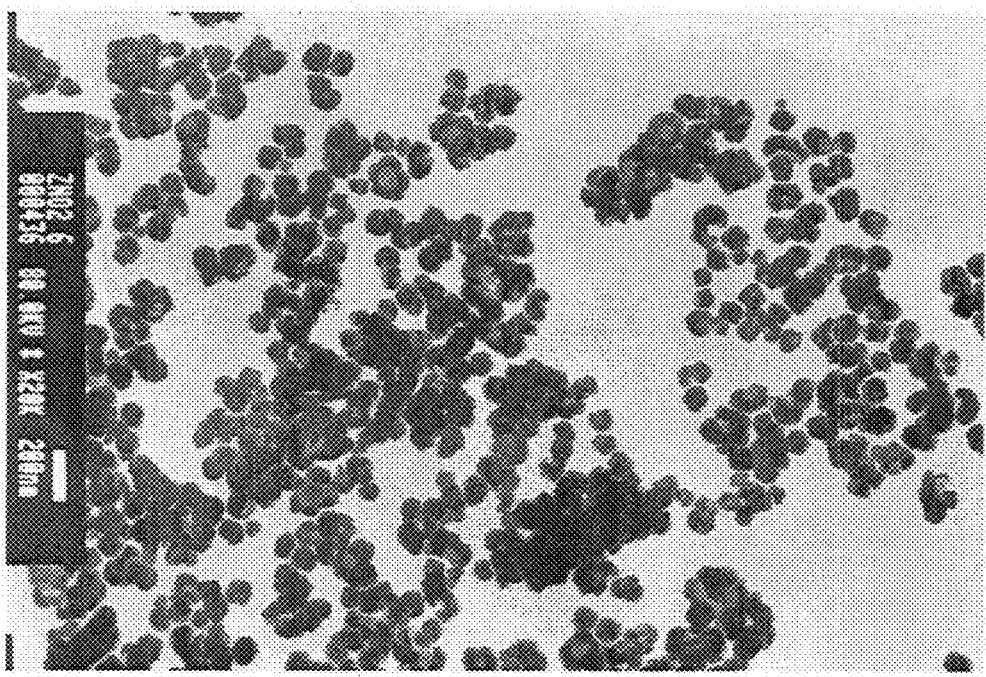
FIG. 1 is a transmission electron microscope photograph of rounded zinc peroxide particles of the present invention obtained in Example 1.

The present invention will be described in detail hereinafter.

The zinc peroxide particles of the present invention are rounded zinc peroxide particles having an average particle diameter of 0.04 μm or more and an aspect ratio of 2.0 or less. Conventional zinc peroxide particles tend to be fine particles, and those having a particle diameter of less than 0.04 μm can be easily produced, but those having any larger particle diameter cannot be produced.

It is an object of the present invention to solve the above-mentioned problem to provide rounded zinc peroxide particles having an average particle diameter of 0.04 μm or more.

The average particle diameter is more preferably 0.045 μm or more, further preferably 0.05 μm or more. The upper limit of the average particle diameter is not particularly limited, but is preferably 100 μm or less, more preferably 50 μm or less.

In the present invention, the average particle diameter of rounded zinc peroxide particles is a particle diameter (μm) defined by a unidirectional diameter in a visual field of 2000 to 100000 magnification in a transmission electron microscope (TEM, JEM-1200EX II, manufactured by JEOL Ltd.) photograph (distance between two parallel lines in a fixed direction with a particle held therebetween; measurements are made in a fixed direction regardless of shapes of particles on the image), and is obtained by measuring the unidirectional diameters of 250 particles in the TEM photograph and determining an average value of a cumulative distribution thereof.

The rounded zinc peroxide particles of the present invention preferably have an aspect ratio of 2.0 or less. Rounded zinc oxide particles formed by thermally decomposing rounded zinc peroxide particles having an aspect ratio of 2.0 or less are preferable because particularly excellent visible light transparency is achieved particularly when the rounded zinc oxide particles are used for a cosmetic. The aspect ratio is more preferably 1.8 or less, further preferably 1.5 or less.

In the present invention, the term "rounded" means that the shape is rounded as a whole, and refers to a spherical shape, an oval shape or the like.

In the present invention, an aspect ratio of the rounded zinc peroxide particles is a ratio between the lengths of a major axis and a minor axis passing through the center of the major axis: major axis/minor axis in a visual field of 2000 to 100000 magnification in a transmission electron microscope (TEM, JEM-1200EX II, manufactured by JEOL Ltd.) photograph, and is obtained by measuring the aspect ratio for 250 particles in the TEM photograph and determining an average value of a cumulative distribution thereof.

Rounded zinc peroxide particles having such an average particle diameter can be obtained by, for example, treating zinc oxide particles as a raw material (hereinafter, referred to as "raw material zinc oxide particles") in an aqueous hydrogen peroxide solution although the method for production thereof is not particularly limited. The method for treating raw material zinc oxide particles in an aqueous hydrogen peroxide solution is not particularly limited, and examples thereof may include a method in which raw material zinc oxide particles are repulped in water to prepare a slurry of raw material zinc oxide particles in a concentration of 10 to 2000 g/l in terms of zinc oxide, an aqueous hydrogen peroxide solution in a concentration of 1 to 500 g/l in terms of hydrogen peroxide is added to the slurry, and the mixture is stirred. When an aqueous hydrogen peroxide solution is added to the slurry of raw material zinc oxide particles and the mixture is treated, the concentration of the raw material zinc oxide particles is preferably 10 to 1500 g/l based on the total amount of the slurry. The treatment amount of hydrogen peroxide is preferably 0.7 times or more, more preferably an equivalent amount or more in terms of the number of moles relative to zinc oxide as a raw material.

In production of rounded zinc peroxide particles as described above, raw material zinc oxide particles are used. The raw material zinc oxide particles are not particularly limited, but the particle diameter is preferably 0.01 μm or more. The particle diameter of the raw material zinc oxide particle corresponds to the diameter of a sphere having the same surface area as a specific surface area determined by a BET method. That is, the particle diameter of the raw material zinc oxide particle is a value determined by the following calculation formula from a specific surface area: Sg determined by making a measurement using a fully automatic BET specific surface area measuring device Macsorb (manufactured by Mountech Co., Ltd.), and a true specific gravity of zinc oxide: ρ.

particle diameter (μm)=[6/($Sg \times \rho$)]

($Sg$ (m$^2$/g): specific surface area, ρ (g/cm$^3$): true specific gravity of particle)

It is to be noted that as the true specific gravity of particle: β, a value of 5.6, which is a value of the true specific gravity of zinc oxide, was used for the above calculation.

Raw material zinc oxide particles that can be used as a raw material are not particularly limited, and zinc oxide produced by a known method can be used. Examples of those that are commercially available may include FINEX-75, FINEX-50, FINEX-30, Fine zinc oxide, SF-15, Zinc oxide No. 1, and the like manufactured by Sakai Chemical Industry Co., Ltd.

Since rounded zinc peroxide particles obtained by treating the raw material zinc oxide particles with hydrogen peroxide have higher uniformity in the particle shape and the particle diameter distribution than the raw material zinc oxide particles, zinc oxide particles as a raw material to be used may have low uniformity in the particle shape and the particle diameter distribution.

The particle diameter, the shape and the like of raw material zinc oxide particles are not particularly limited, and may be appropriately selected according to physical properties of the intended zinc peroxide. Examples of the particle shape may include a needle shape, a rod shape, a plate shape and a spherical shape. That is, according to the production method of the present invention, rounded zinc peroxide particles having an aspect ratio of 2.0 or less can be obtained regardless of the shape of raw material zinc oxide particles.

The particle diameter of raw material zinc oxide particles is not particularly limited, but for obtaining rounded zinc peroxide particles having an average particle diameter of 0.04 μm or more according to the present invention, it is preferable to use raw material zinc oxide particles having a particle diameter of 0.01 μm or more. In the production method of the present invention, the average particle diameter of rounded zinc peroxide particles obtained after hydrogen peroxide treatment can be arbitrarily controlled by the particle diameter of raw material zinc oxide particles.

The treatment temperature and the treatment time of the hydrogen peroxide treatment in the present invention are not particularly limited, and mention may be made of, for example, conditions of treatment temperature: 10 to 100° C. and treatment time: 0.5 to 12 hours. In the treatment described above, additives such as a dispersant may be added as necessary within the bounds of not impairing the object of the present invention.

Rounded zinc peroxide particles thus obtained may be subjected to post-treatments such as filtration, water washing and drying as necessary. The rounded zinc peroxide particles may be classified by sieving as necessary. Examples of methods for classification by sieving may include wet classification and dry classification. Further, a treatment such as wet crushing or dry crushing may be performed.

The rounded zinc peroxide particles of the present invention can also be used as a raw material of rounded zinc oxide particles. That is, rounded zinc peroxide particles as described above can be calcinated at 220 to 700° C. and thereby thermally decomposed to form rounded zinc oxide particles. Rounded zinc oxide particles obtained by the above-mentioned production method have such a nature that the particle shape and the particle size are uniform and aggregation of particles is hard to occur as compared to raw material zinc oxide particles used as a raw material. Therefore, the rounded zinc oxide particles can be suitably used as a cosmetic and a heat releasing filler. The above-mentioned rounded zinc oxide particles are a part of the present invention.

The average particle diameter of the rounded zinc oxide particles of the present invention is preferably 0.04 μm or more. The average particle diameter is more preferably 0.045 μm or more, further preferably 0.05 μm or more. The average particle diameter of the rounded zinc oxide particles is preferably 10 μm or less, more preferably 1 μm or less although the upper limit of the particle diameter is not particularly limited.

In the present invention, the average particle diameter of rounded zinc oxide particles is a particle diameter (μm) defined by a unidirectional diameter in a visual field of 2000 to 100000 magnification in a transmission electron microscope (TEM, JEM-1200EX II, manufactured by JEOL Ltd.) photograph (distance between two parallel lines in a fixed direction with a particle held therebetween; measurements are made in a fixed direction regardless of shapes of particles on the image), and is obtained by measuring the unidirectional diameters of 250 particles in the TEM photograph and determining an average value of a cumulative distribution thereof.

The rounded zinc oxide particles of the present invention preferably have an aspect ratio of 2.0 or less. An aspect ratio of 2.0 or less is preferable because particularly excellent dispersibility and transparency can be achieved particularly when the rounded zinc oxide particles are used for a cosmetic. An aspect ratio of 2.0 or less is preferable also because when the rounded zinc oxide particles are used for a heat releasing filler, the filling rate of the filler can be increased. The aspect ratio is more preferably 1.8 or less, further preferably 1.5 or less.

In the present invention, an aspect ratio of the rounded zinc oxide particles is a ratio between the lengths of a major axis and a minor axis passing through the center of the major axis:

major axis/minor axis in a visual field of 2000 to 100000 magnification in a transmission electron microscope (TEM, JEM-1200EX II, manufactured by JEOL Ltd.) photograph, and is obtained by measuring the aspect ratio for 250 particles in TEM photograph and determining an average value of a cumulative distribution thereof.

Further, the rounded zinc oxide particles of the present invention preferably have a specific surface area of 30 m$^2$/g or less as measured by the BET method. The specific surface area is more preferably 28 m$^2$/g or less, further preferably 27 m$^2$/g or less. A specific surface area within the above-described range is preferable because principally rounded zinc oxide particles having an average particle diameter of 0.04 μm or more are obtained.

The rounded zinc oxide particles of the present invention preferably have a D90/D10 of 3.0 or less in particle size distribution.

In the above-described parameter, D10 denotes a 10% cumulative particle diameter on the volume basis, and D90 denotes a 90% cumulative particle diameter on the volume basis. That is, when the D90/D10 is 3.0 or less, the number of coarse particles having an extremely large particle diameter and fine particles having an extremely small particle diameter, as compared to the average particle diameter, is small.

Since rounded zinc oxide particles, the D90/D10 of which is 3.0 or less, have a small number of extremely large coarse particles and extremely small fine particles as compared to the average particle diameter, and have a very sharp particle size distribution, the rounded zinc oxide particles are especially preferable when used for a cosmetic because excellent visible light transparency can be stably achieved.

D10 and D90 of the rounded zinc oxide particles are values measured by a laser diffraction/scattering particle size distribution measuring device LA-750 (manufactured by HORIBA, Ltd.). In a mayonnaise bottle having a volume of 75 ml, 0.5 g of the rounded zinc oxide particles, 20 ml of an aqueous sodium hexametaphosphate solution in a concentration of 0.025% by weight in terms of sodium hexametaphosphate, and 88 g of zirconia beads of 0.3 mm φ (manufactured by Toray Industries, Inc., crushing balls) were put and sufficiently mixed, the mixture was then fixed in Paint conditioner Model 5410 (manufactured by Red Devil, Inc.), and subjected to a dispersion treatment by giving vibrations for 45 minutes to thereby prepare a slurry, and a measurement was performed using the slurry. The measurement was performed with the relative refractive index set at 1.5.

The method and device for performing the calcinating as mentioned above are not particularly limited, and the calcinating can be performed using any known method. Examples may include a method of performing calcinating in a stationary furnace or a rotary furnace.

When zinc oxide is used in various kinds of applications, the surface may be subjected to a silica treatment, an alumina treatment, a zirconia treatment or the like to coat the surface. When the rounded zinc oxide particles of the present invention are subjected to the above-mentioned surface coating treatment, it is preferable to obtain surface-coated rounded zinc oxide particles by surface-coating a zinc peroxide powder with a silicon compound, an aluminum compound, a zirconium compound or the like, and calcinating the surface-coated particles. The surface-coated rounded zinc oxide particles thus obtained are preferable because aggregation of particles is hard to occur, and the particle diameter and the particle distribution are controlled. Rounded zinc oxide particles obtained by calcinating rounded zinc peroxide particles which have not been surface-treated can also be surface-treated.

The method for surface-treating rounded zinc peroxide particles or rounded zinc oxide particles obtained by calcinating rounded zinc peroxide particles is not particularly limited, and the surface treatment can be performed using, for example, a method described in detail below.

When a silica coating is formed in the surface treatment according to the present invention, a high-density coating layer is obtained which contains a silicon oxide in an amount of 0.1 to 20% by weight, preferably 0.2 to 15% by weight, with respect to rounded zinc peroxide particles or rounded zinc oxide particles obtained by calcinating rounded zinc peroxide particles. The silicon oxide is not particularly limited, but is preferably hydrous silica. When the ratio of the silicon oxide in a rounded zinc peroxide particle composition or a rounded zinc oxide particle composition obtained by calcinating rounded zinc peroxide particles is less than 0.1% by weight, the surface activity of the rounded zinc peroxide particles or the rounded zinc oxide particles cannot be sufficiently suppressed. On the other hand, when the ratio of the silicon oxide is more than 20% by weight, the content of zinc oxide in a rounded zinc oxide particle composition, which is formed by calcinating the obtained rounded zinc peroxide particle composition, decreases, so that sufficient ultraviolet blocking performance cannot be achieved. When the alumina treatment, the zirconia treatment or the like is performed, a similar method can be used.

Calcinating of rounded zinc peroxide particles subjected to the surface treatment can be performed using a method similar to the above-described method of calcinating rounded zinc peroxide particles.

When the rounded zinc peroxide particles and rounded zinc oxide particles of the present invention are those subjected to the above-mentioned surface treatment, various kinds of parameters such as the particle diameter and particle size distribution are preferably within the range of the values for the rounded zinc peroxide particles and rounded zinc oxide particles described above.

The rounded zinc oxide particles (including the above-described surface-coated rounded zinc oxide particles) of the present invention may be surface-treated after calcinating. The surface treatment is not particularly limited, and examples may include surface treatments with a surface treatment agent selected from an organic silicon compound, an organic aluminum compound, an organic titanium compound, a higher fatty acid, a higher fatty acid ester, a metallic soap, a polyhydric alcohol and an alkanolamine. The treatment amount of the surface treatment agent can be appropriately set according to the particle diameter of the rounded zinc oxide particles or surface-coated rounded zinc oxide particles.

The rounded zinc oxide particles of the present invention can be used as component compounded in a cosmetic. Such a cosmetic is a part of the present invention. The rounded zinc oxide particles of the present invention can be suitably used in a cosmetic because they are excellent in transparency because of the small aspect ratio, and exhibit excellent performance in ultraviolet blocking performance.

Examples of the cosmetic of the present invention may include a foundation, a makeup base, an eye shadow, a rouge, a mascara, a lipstick and a sunscreen agent. The cosmetic of the present invention can be in any form such as that of an oily cosmetic, an aqueous cosmetic, an O/W type cosmetic or a W/O type cosmetic. Above all, the cosmetic of the present invention can be particularly suitably used in sunscreen agents.

For the cosmetic of the present invention, any aqueous component or oily component that can be used in the field of cosmetics can be used in combination in addition to components that form the above-described mixture. The aqueous component and oily component described above are not particularly limited, and examples thereof may include those containing components such as oils, surfactants, moisturizers, higher alcohols, sequestrants, natural and synthetic polymers, water-soluble and oil-soluble polymers, UV blocking agents, various extracts, various powders including inorganic and organic pigments and inorganic and organic clay minerals, inorganic and organic pigments treated with metallic soap or silicone, coloring materials such as organic dyes, preservatives, antioxidants, dyes, thickeners, pH adjusters, perfumes, cooling-sensation agents, antiperspirants, disinfectants, and skin activators. Specifically, a desired cosmetic can be produced in the usual manner using any one or more of the components listed below. The amounts of these components incorporated are not particularly restricted as long as they do not interfere with the effects of the present invention.

The oil is not particularly limited, and examples thereof may include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, arachis oil, tea seed oil, kaya oil, rice bran oil, Chinese tung oil, Japanese tung oil, jojoba oil, germ oil, triglycerol, glycerol trioctanoate, glycerol triisopalmitate, cacao butter, coconut oil, horse fat, hydrogenated coconut oil, palm oil, beef tallow, mutton tallow, hydrogenated beef tallow, palm kernel oil, lard, beef bone fat, Japan wax kernel oil, hydrogenated oil, neatsfoot oil, Japan wax, hydrogenated castor oil, beeswax, candelilla wax, cotton wax, carnauba wax, bayberry wax, insect wax, spermaceti wax, montan wax, bran wax, lanolin, kapok wax, lanolin acetate, liquid lanolin, sugarcane wax, isopropyl lanolate, hexyllaurate, reduced lanolin, jojoba wax, hard lanolin, shellac wax, POE lanolin alcohol ether, POE lanolin alcohol acetate, POE cholesterol ether, polyethylene glycol lanolate, POE hydrogenated lanolin alcohol ether, liquid paraffin, ozokerite, pristane, paraffin, ceresin, squalene, Vaseline, and microcrystalline wax.

The lipophilic nonionic surfactant is not particularly limited, and examples thereof may include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerin polyglycerin fatty acids such as glycerol mono-cottonseed oil fatty acid, glycerol monoerucate, glycerol sesquioleate, glycerol monostearate, $\alpha,\alpha'$-glycerol oleate pyroglutamate, and glycerol monostearate malate; propylene glycol fatty acid esters such as propylene glycol monostearate; hydrogenated castor oil derivatives; and glycerol alkyl ethers.

The hydrophilic nonionic surfactant is not particularly limited, and examples thereof may include POE sorbitan fatty acid esters such as POE sorbitan monooleate, POE sorbitan monostearate, and POE sorbitan tetraoleate; POE sorbitol fatty acid esters such as POE sorbitol monolaurate, POE sorbitol monooleate, POE sorbitol pentaoleate and POE sorbitol monostearate; POE glycerin fatty acid esters such as POE glycerin monostearate, POE glycerin monoisostearate and POE glycerin triisostearate; POE fatty acid esters such as POE monooleate, POE distearate, POE monodioleate and ethylene glycol distearate; POE alkyl ethers such as POE lauryl ether, POE oleyl ether, POE stearyl ether, POE behenyl ether, POE 2-octyldodecyl ether and POE cholestanol ether; POE alkyl phenyl ethers such as POE octyl phenyl ether, POE nonyl phenyl ether and POE dinonyl phenyl ether; Pluaronic types such as Pluronic; POE/POP alkyl ethers such as POE/POP cetyl ether, POE/POP 2-decyltetradecyl ether, POE/POP monobutyl ether, POE/POP hydrogenated lanolin and POE/POP glycerin ether; tetra-POE/tetra-POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester and POE hydrogenated castor oil maleic acid; POE beeswax/lanolin derivatives such as POE sorbitol beeswax; alkanolamides such as coconut oil fatty acid diethanolamide, lauric acid monoethanolamide and fatty acid isopropanol amide; POE propylene glycol fatty acid esters; POE alkylamines; POE fatty acid amides; sucrose fatty acid esters; POE nonylphenyl formaldehyde condensation products; alkyl ethoxy dimethylamine oxides; and trioleyl phosphoric acid.

Examples of other surfactants include anionic surfactants such as fatty acid soaps, higher-alkyl sulfuric ester salts, POE triethanolamine lauryl sulfate, and alkyl ether sulfuric ester salts; cationic surfactants such as alkyl trimethylammonium salts, alkyl pyridinium salts, alkyl quaternary ammonium salts, alkyl dimethylbenzyl ammonium salts, POE alkylamines, alkylamine salts, and polyamine fatty acid derivatives; and amphoteric surfactants such as imidazoline amphoteric surfactants and betaine surfactants. They may be incorporated within the bounds of not causing any problems with stability and skin irritation.

The moisturizer is not particularly limited, and examples thereof may include xylitol, sorbitol, maltitol, chondroitin sulfate, hyaluronic acid, mucoitinsulfuric acid, caronic acid, atelocollagen, cholesteryl-12-hydroxystearate, sodium lactate, bile salts, dl-pyrrolidone carboxylate, short-chain soluble collagens, diglycerol (EO) PO adducts, Rosa roxburghii extract, yarrow extract, and melilot extract.

The higher alcohol is not particularly limited, and examples thereof may include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerol ether (batyl alcohol), 2-decyltetradecynol, lanolin alcohol, cholesterol, phytosterol, hexyldodecanol, isostearyl alcohol, and octyldodecanol.

The sequestrant is not particularly limited, and examples thereof may include 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

The natural water-soluble polymer is not particularly limited, and examples thereof may include plant-derived polymers such as gum arabic, tragacanth gum, galactan, guar gum, carob gum, karaya gum, carrageenan, pectin, agar, quince seed (quince), algal colloid (algal extract), starch (rice, corn, potato, wheat), and glycyrrhizinic acid; microorganism-derived polymers such as xanthan gum, dextran, succinoglucan, and pullulan; and animal-derived polymers such as collagen, casein, albumin, and gelatin.

The semisynthetic water-soluble polymer is not particularly limited, and examples thereof may include starch polymers such as carboxymethyl starch and methyl hydroxypropyl starch; cellulose polymers such as methyl cellulose, nitro cellulose, ethyl cellulose, methyl hydroxypropyl cellulose, hydroxyethyl cellulose, cellulose sodium sulfate, hydroxypropyl cellulose, sodium carboxymethylcellulose (CMC), crystalline cellulose, and cellulose powder; and alginate polymers such as sodium alginate and propylene glycol alginate.

The synthetic water-soluble polymer is not particularly limited, and examples thereof may include vinyl polymers such as polyvinyl alcohol, polyvinyl methyl ether, and polyvinyl pyrrolidone; polyoxyethylene polymers such as polyethylene glycol 20,000, polyethylene glycol 40,000, and polyethylene glycol 60,000; copolymers such as polyoxyethylene-polyoxypropylene copolymers; acrylic polymers such as sodium polyacrylate, polyethylacrylate, and polyacrylamide; polyethyleneimine; and cationic polymers.

The inorganic water-soluble polymer is not particularly limited, and examples thereof may include bentonite, magnesium aluminum silicate (Veegum), laponite, hectorite, and silicic anhydride.

The ultraviolet blocking agent is not particularly limited, and examples thereof may include benzoic acid-based ultraviolet blocking agents such as paraminobenzoic acid (hereinafter, abbreviated as PABA), PABA monoglycerin ester, N,N-dipropoxy PABA ethyl ester, N,N-diethoxy PABA ethyl ester, N,N-dimethyl PABA ethyl ester and N,N-dimethyl PABA butyl ester; anthranilic acid-based ultraviolet blocking agents such as homomethyl-N-acetyl anthranilate; salicylic acid-based ultraviolet blocking agents such as amyl salicylate, menthyl salicylate, homomethyl salicylate, octyl salicylate, phenyl salicylate, benzyl salicylate and p-isopropanol phenyl salicylate; cinnamic acid-based ultraviolet blocking agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate and glycerylmono-2-ethylhexanoyl-di-paramethoxy cinnamate; benzophenone-based ultraviolet blocking agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl benzotriazole, dibenzalazine, dianisoylmethane, 4-methoxy-4'-t-butyldibenzoylmethane and 5-(3,3-dimethyl-2-norbornylidene)-3-pentane-2-one.

Other chemical components are not particularly limited, and examples thereof may include vitamins such as vitamin A oil, retinol, retinol palmitate, inositol, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), DL-α-tocopherol, DL-α-tocopherol acetate, pantothenic acid, and biotin; hormones such as estradiol and ethynyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor, sulfur, lysozyme chloride, and pyridoxine chloride.

Various kinds of extracts are not particularly limited, and examples thereof may include Houttuynia cordata extract, Phellodendron bark extract, melilot extract, dead nettle extract, licorice extract, peony root extract, soapwort extract, luffa extract, cinchona extract, strawberry geranium extract, sophora root extract, nuphar extract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, hamamelis extract, placenta extract, thymic extract, silk extract, and licorice extract.

Examples of the various kinds of powders may include bright coloring pigments such as red oxide, yellow iron oxide, black iron oxide, mica titanium, iron oxide-coated mica titanium and titanium oxide-coated glass flakes, inorganic powders such as those of mica, talc, kaolin, sericite, titanium dioxide and silica, and organic powders such as polyethylene powder, nylon powder, crosslinked polystyrene, cellulose powder and silicone powder. Preferably, part or all of the powder component is subjected to a hydrophobization treatment with a substance such as a silicone, a fluorine compound, a metallic soap, an oily agent or an acyl glutamic acid salt for improvement of sensory characteristics and improvement of makeup retainability. Other zinc oxide particles that do not fall under the present invention may be mixed and used.

The rounded zinc oxide particles of the present invention can also be used as a heat releasing filler.

When the rounded zinc oxide particles of the present invention are used as a heat releasing filler, they may be used either alone or in combination with other heat releasing fillers. It is preferable to use the heat releasing filler of the present invention at a ratio of 10 to 90% by volume based on the total amount of a heat releasing composition such as a resin composition or a grease composition regardless of whether it is used alone or used in combination with other heat releasing fillers.

The rounded zinc oxide particles of the present invention can also be used in combination with a heat releasing filler having a different particle diameter when used as a heat releasing filler. The heat releasing filler that can be used in combination is not particularly limited, and examples thereof may include metal oxides such as magnesium oxide, titanium oxide and aluminum oxide, aluminum nitride, boron nitride, silicon carbide, silicon nitride, titanium nitride, metal silicon and diamond. Further, zinc oxide other than the rounded zinc oxide particles described above can be used in combination. The heat releasing filler used in combination may have any shape such as a spherical shape, a needle shape, a rod shape or a plate shape.

When the rounded zinc oxide particles are used as a heat releasing filler, they can be mixed with a resin and used as a heat releasing resin composition. In this case, the resin to be used may be either a thermoplastic resin or a thermosetting resin, and examples thereof may include resins such as an epoxy resin, a phenol resin, a polyphenylene sulfide (PPS) resin, a polyester-based resin, polyamide, polyimide, polystyrene, polyethylene, polypropylene, polyvinyl chloride, polyvinylidene chloride, a fluororesin, polymethyl methacrylate, an ethylene/ethyl acrylate copolymer (EEA) resin, polycarbonate, polyurethane, polyacetal, polyphenylene ether, polyether imide, an acrylonitrile-butadiene-styrene copolymer (ABS) resin, a liquid crystal resin (LCP), a silicone resin and an acrylic resin.

The heat releasing resin composition of the present invention may be (1) a resin composition for thermoforming, which is obtained by kneading a thermoplastic resin and the rounded zinc oxide particles in a molten state, or (2) a resin composition obtained by kneading a thermosetting resin and the rounded zinc oxide particles, followed by heating the mixture to be cured, or (3) a resin composition for coatings, which is obtained by dispersing the rounded zinc oxide particles in a resin solution or dispersion.

When the heat releasing resin composition of the present invention is a resin composition for thermoforming, a resin component can be freely selected according to a use purpose. For example, when the resin composition is bonded and adhered to a heat source and a radiator plate, a resin having high adhesiveness and a low hardness, such as a silicone resin or an acrylic resin, may be selected.

When the heat releasing resin composition of the present invention is a resin composition for coatings, the resin does not necessarily have to have curability. The coating may be a solvent-based coating containing an organic solvent, or a water-based coating with a resin dissolved or dispersed in water.

When the rounded zinc oxide particles are used as a heat releasing filler, they can be mixed with a base oil containing a mineral oil or a synthetic oil, and used as a heat releasing grease. When the rounded zinc oxide particles are used as the heat releasing grease, an α-olefin, a diester, a polyol ester, a trimellitic acid ester, a polyphenyl ether, an alkyl phenyl ether or the like can be used as a synthetic oil. The rounded zinc oxide particles can also be mixed with a silicone oil and used as a heat releasing grease.

When the rounded zinc oxide particles of the present invention are used as a heat releasing filler, other components can be used in combination. Examples of other components that can be used in combination may include heat releasing fillers other than zinc oxide, such as metal oxides such as magnesium oxide, titanium oxide and aluminum oxide, aluminum nitride, boron nitride, silicon carbide, silicon nitride, titanium nitride, metal silicon, and diamond; resins; and surfactants.

When the rounded zinc oxide particles of the present invention are used in combination with zinc oxide particles having a smaller particle diameter and other heat releasing fillers, more excellent heat releasing performance can be achieved. The zinc oxide particles used in combination, which have a small particle diameter, preferably have a shape such as a spherical shape, a needle shape, a rod shape or a plate shape.

The rounded zinc oxide particles of the present invention can be used in the fields of vulcanization accelerators for rubber, pigments for coatings/inks, electronic components such as ferrites and varistors, pharmaceuticals and so on in addition to the cosmetics and heat releasing fillers described above.

EXAMPLES

Hereinafter, the present invention will be explained with reference to examples. However, the present invention is not limited to these examples.

Example 1

Figure 2:
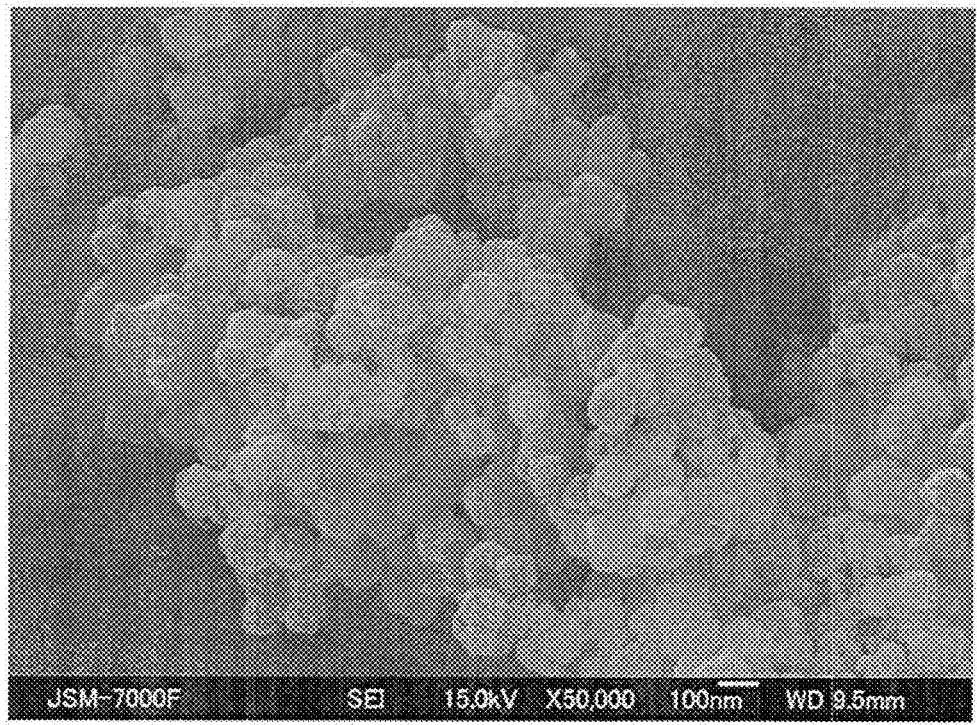
FIG. 2 is a scanning electron microscope photograph of rounded zinc peroxide particles of the present invention obtained in Example 1.
Figure 3:
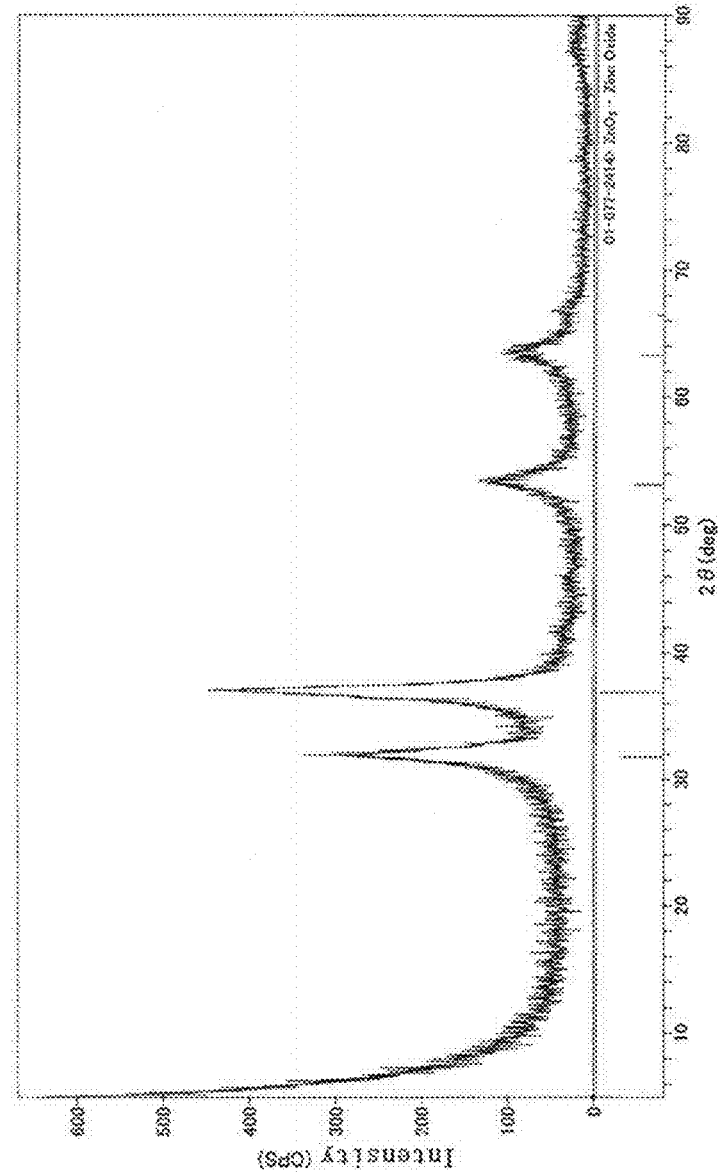
FIG. 3 is an X-ray diffraction spectrum of rounded zinc peroxide particles of the present invention obtained in Example 1.

In water was repulped 16.28 g of SF-15 (manufactured by Sakai Chemical Industry Co., Ltd., particle diameter: 0.08 μm) to prepare 500 ml of a slurry in a concentration of 0.4 mol/l in terms of zinc oxide. Subsequently, 20.77 g of hydrogen peroxide water (manufactured by Wako Pure Chemical Industries, Ltd.; content of hydrogen peroxide: 30.0 to 35.5% by weight) was added to water to prepare 500 ml an aqueous hydrogen peroxide solution in a concentration of 0.4 mol/l in terms of hydrogen peroxide. Subsequently, 500 ml of the slurry of SF-15 was stirred, 500 ml of the aqueous hydrogen peroxide solution was added thereto, and the mixture was subjected to a stirring treatment for 6 hours with the treatment temperature set at 25° C. After the stirring treatment, the mixture was filtrated, washed with water, and dried at 110° C. for 12 hours to obtain rounded zinc peroxide particles having an average particle diameter of 0.11 μm. The size and form of the obtained particles were observed with a transmission electron microscope (TEM, JEM-1200EX II, manufactured by JEOL Ltd.). The obtained electron microscope photograph is shown in FIG. 1. An observation was made with a scanning electron microscope (SEM, JSM-7000F, manufactured by JEOL Ltd.). The obtained electron microscope photograph is shown in FIG. 2. Further, the X-ray diffraction spectrum of the obtained particles is shown in FIG. 3. The results of evaluating the physical properties of the obtained particles are shown in Table 1.

Example 2

Figure 4:
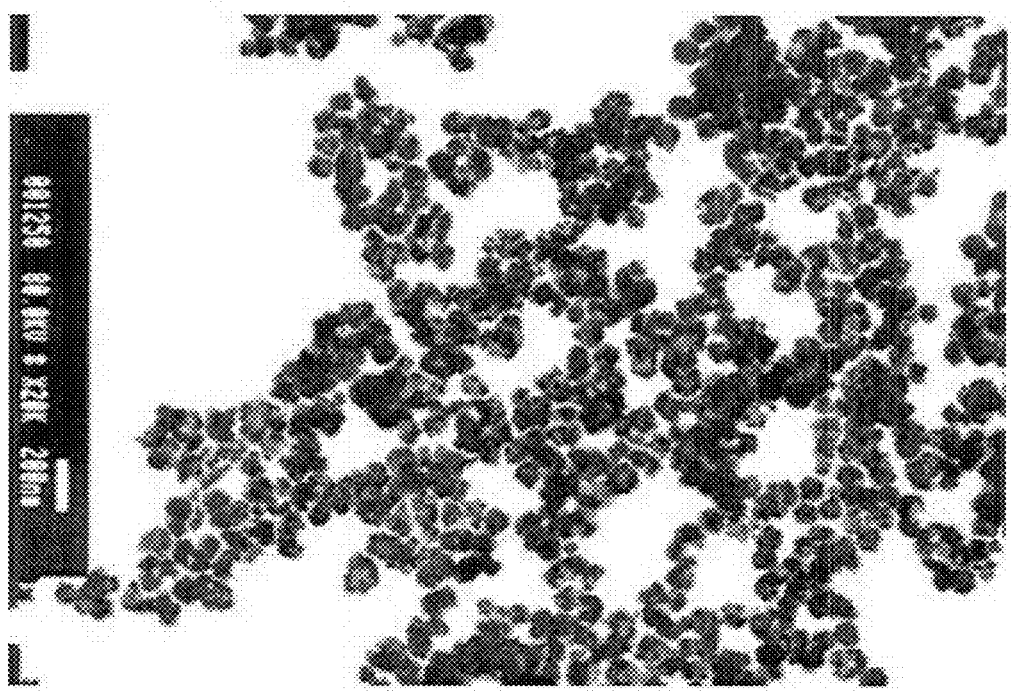
FIG. 4 is a transmission electron microscope photograph of rounded zinc oxide particles of the present invention obtained in Example 2.
Figure 5:
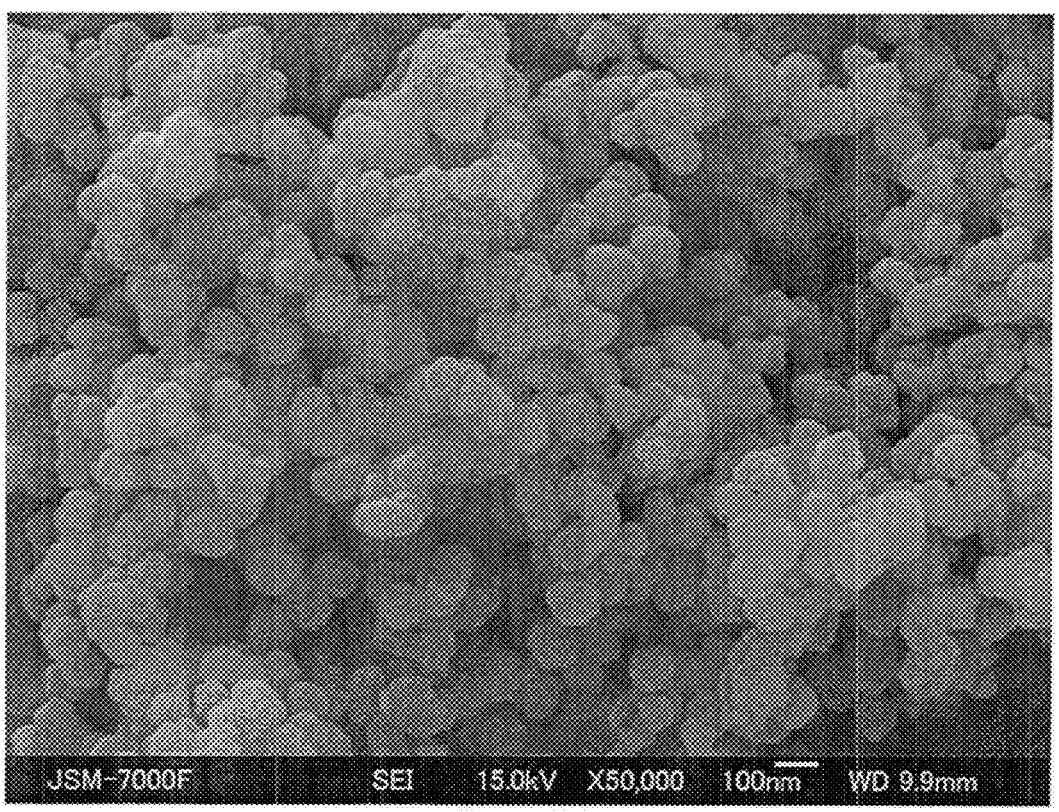
FIG. 5 is a scanning electron microscope photograph of rounded zinc oxide particles of the present invention obtained in Example 2.
Figure 6:
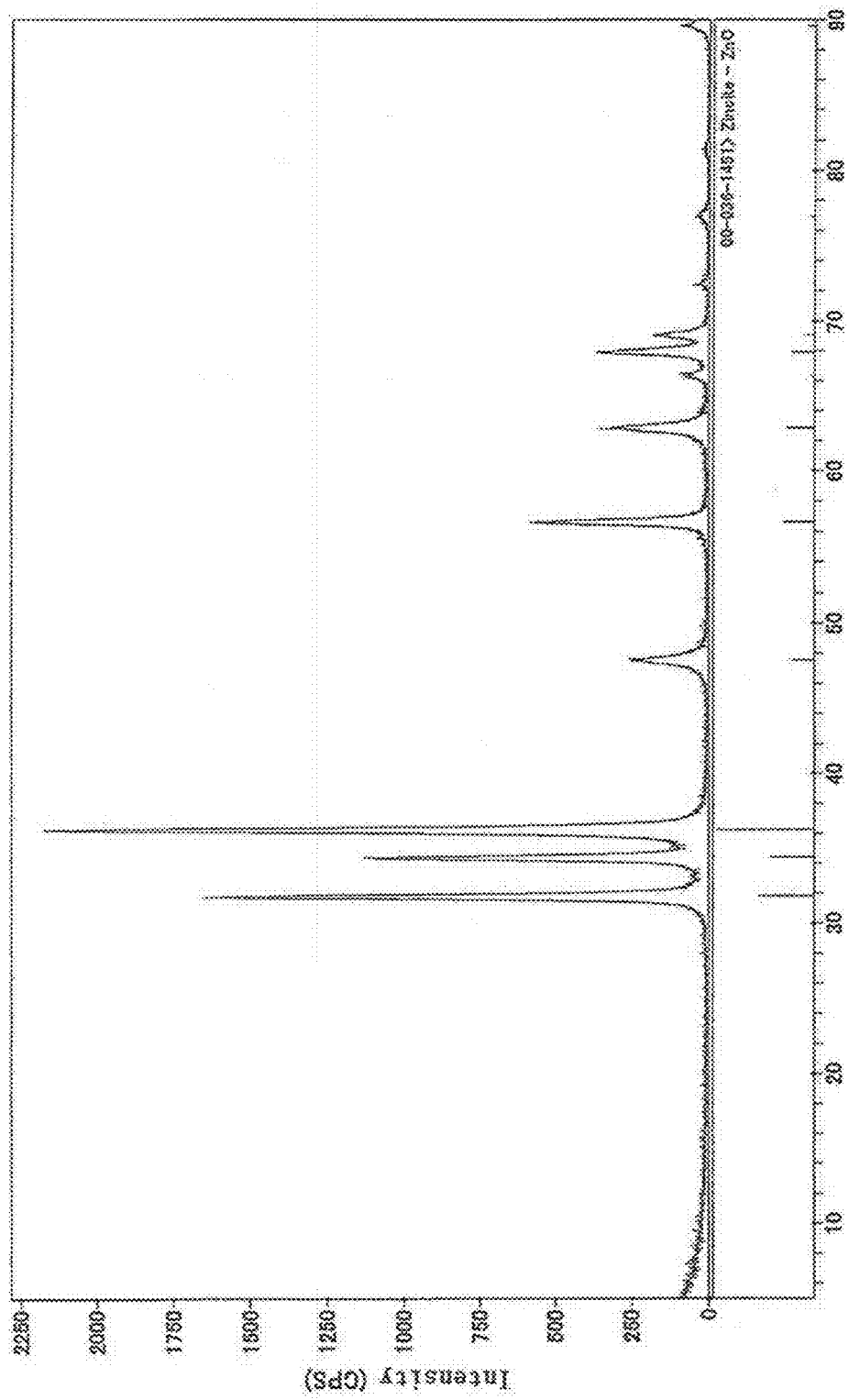
FIG. 6 is an X-ray diffraction spectrum of rounded zinc oxide particles of the present invention obtained in Example 2.

In an alumina crucible (length/width/height=100 mm/100 mm/35 mm) were put 10 g of the rounded zinc peroxide particles obtained in Example 1, and the particles were left standing and calcinated at 500° C. for 2 hours in an electric muffle furnace (manufactured by TOYO ENGINEERING WORKS, LTD.) to obtain rounded zinc oxide particles having an average particle diameter of 0.10 μm. The size and form of the obtained particles were observed with a transmission electron microscope (TEM, JEM-1200EX II, manufactured by JEOL Ltd.). The obtained electron microscope photograph is shown in FIG. 4. An observation was made with a scanning electron microscope (SEM, JSM-7000F, manufactured by JEOL Ltd.). The obtained electron microscope photograph is shown in FIG. 5. Further, the X-ray diffraction spectrum of the obtained particles is shown in FIG. 6. The results of evaluating the physical properties of the obtained particles and the physical properties of the coating film are shown in Table 1.

Example 3

Figure 7:
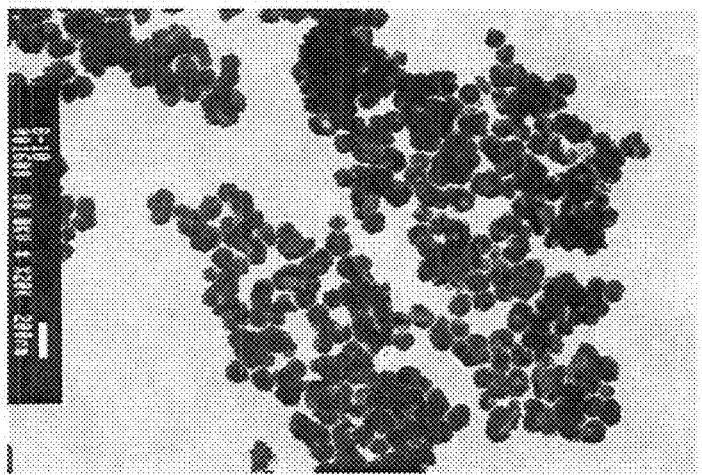
FIG. 7 is a transmission electron microscope photograph of rounded zinc peroxide particles of the present invention obtained in Example 3.

In water was repulped 16.28 g of Fine zinc oxide (manufactured by Sakai Chemical Industry Co., Ltd., particle diameter: 0.11 μm) to prepare 500 ml of a slurry in a concentration of 0.4 mol/l in terms of zinc oxide. Subsequently, 20.77 g of hydrogen peroxide water (manufactured by Wako Pure Chemical Industries, Ltd.; content of hydrogen peroxide: 30.0 to 35.5% by weight) was added to water to prepare 500 ml an aqueous hydrogen peroxide solution in a concentration of 0.4 mol/l in terms of hydrogen peroxide. Subsequently, 500 ml of the slurry of fine zinc oxide was stirred, 500 ml of the aqueous hydrogen peroxide solution was added thereto, and the mixture was subjected to a stirring treatment for 6 hours with the treatment temperature set at 25° C. After the stirring treatment, the mixture was filtrated, washed with water, and dried at 110° C. for 12 hours to obtain rounded zinc peroxide particles having an average particle diameter of 0.13 μm. The size and form of the obtained particles were observed with a transmission electron microscope (TEM, JEM-1200EX II, manufactured by JEOL Ltd.). The obtained electron microscope photograph is shown in FIG. 7. The results of evaluating the physical properties of the obtained particles are shown in Table 1.

Example 4

In an alumina crucible (length/width/height=100 mm/100 mm/35 mm) were put 10 g of the rounded zinc peroxide particles obtained in Example 3, and the particles were left standing and calcinated at 500° C. for 2 hours in an electric muffle furnace (manufactured by TOYO ENGINEERING WORKS, LTD.) to obtain rounded zinc oxide particles having an average particle diameter of 0.12 μm. The results of evaluating the physical properties of the obtained particles and the physical properties of the coating film are shown in Table 1.

Example 5

Figure 8:
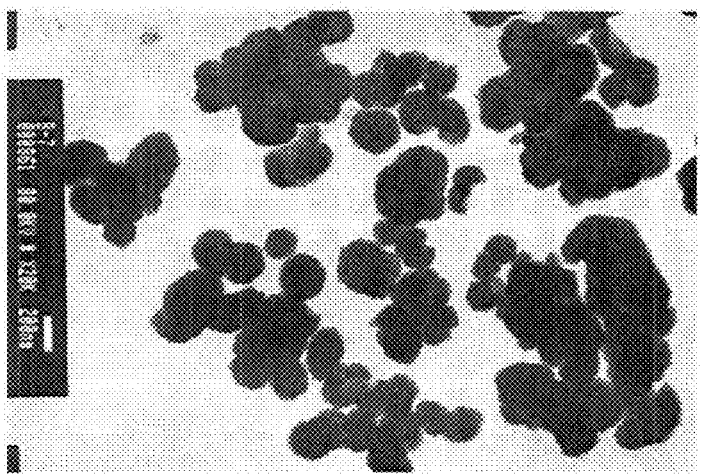
FIG. 8 is a transmission electron microscope photograph of rounded zinc peroxide particles of the present invention obtained in Example 5.

In water was repulped 16.28 g of Zinc oxide No. 1 (manufactured by Sakai Chemical Industry Co., Ltd., particle diameter: 0.31 μm) to prepare 500 ml of a slurry in a concentration of 0.4 mol/l in terms of zinc oxide. Subsequently, 20.77 g of hydrogen peroxide water (manufactured by Wako Pure Chemical Industries, Ltd.; content of hydrogen peroxide: 30.0 to 35.5% by weight) was added to water to prepare 500 ml an aqueous hydrogen peroxide solution in a concentration of 0.4 mol/l in terms of hydrogen peroxide. Subsequently, 500 ml of the slurry of Zinc oxide No. 1 was stirred, 500 ml of the aqueous hydrogen peroxide solution was added thereto, and the mixture was subjected to a stirring treatment for 6 hours with the treatment temperature set at 25° C. After the stirring treatment, the mixture was filtrated, washed with water, and dried at 110° C. for 12 hours to obtain rounded zinc peroxide particles having an average particle diameter of 0.36 μm. The size and form of the obtained particles were observed with a transmission electron microscope (TEM, JEM-1200EX II, manufactured by JEOL Ltd.). The obtained electron microscope photograph is shown in FIG. 8. The results of evaluating the physical properties of the obtained particles are shown in Table 1.

Example 6

Figure 9:
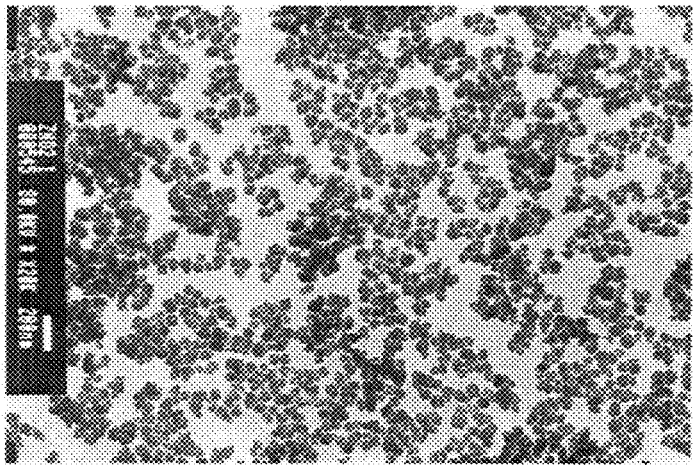
FIG. 9 is a transmission electron microscope photograph of rounded zinc peroxide particles of the present invention obtained in Example 6.

In water was repulped 16.28 g of FINEX-50 (manufactured by Sakai Chemical Industry Co., Ltd., particle diameter: 0.02 μm) to prepare 500 ml of a slurry in a concentration of 0.4 mol/l in terms of zinc oxide. Subsequently, 20.77 g of hydrogen peroxide water (manufactured by Wako Pure Chemical Industries, Ltd.; content of hydrogen peroxide: 30.0 to 35.5% by weight) was added to water to prepare 500 ml an aqueous hydrogen peroxide solution in a concentration of 0.4 mol/l in terms of hydrogen peroxide. Subsequently, 500 ml of the slurry of FINEX-50 was stirred, 500 ml of the aqueous hydrogen peroxide solution was added thereto, and the mixture was subjected to a stirring treatment for 6 hours with the treatment temperature set at 25° C. After the stirring treatment, the mixture was filtrated, washed with water, and dried at 110° C. for 12 hours to obtain rounded zinc peroxide particles having an average particle diameter of 0.05 μm. The size and form of the obtained particles were observed with a transmission electron microscope (TEM, JEM-1200EX II, manufactured by JEOL Ltd.). The obtained electron microscope photograph is shown in FIG. 9. The results of evaluating the physical properties of the obtained particles are shown in Table 1.

Comparative Example 1

Figure 10:
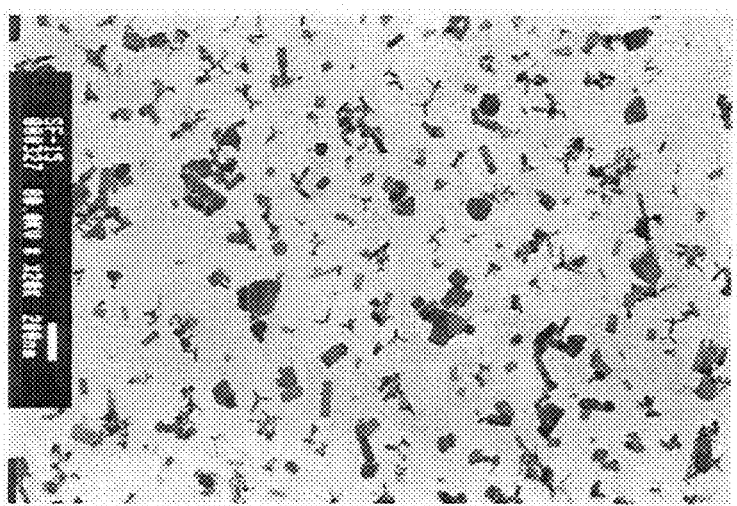
FIG. 10 is a transmission electron microscope photograph of zinc oxide particles (SF-15 manufactured by Sakai Chemical Industry Co., Ltd.) used in Comparative Example 1.

SF-15 (manufactured by Sakai Chemical Industry Co., Ltd., particle diameter: 0.08 μm) was evaluated in the same manner as in the examples. The electron microscope photograph is shown in FIG. 10. The results of evaluating the physical properties of the particles are shown in Table 1.

Comparative Example 2

Figure 11:
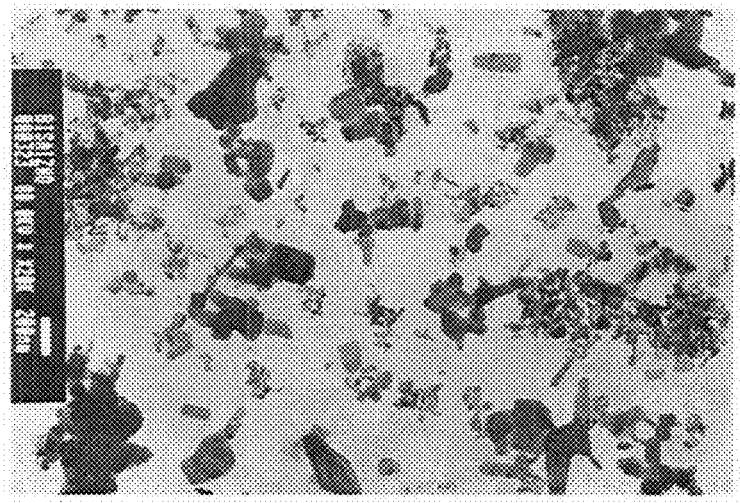
FIG. 11 is a transmission electron microscope photograph of zinc oxide particles (Fine zinc oxide manufactured by Sakai Chemical Industry Co., Ltd.) used in Comparative Example 2.

Fine zinc oxide (manufactured by Sakai Chemical Industry Co., Ltd., particle diameter: 0.11 μm) was evaluated in the same manner as in the examples. The electron microscope photograph is shown in FIG. 11. The results of evaluating the physical properties of the particles and the physical properties of the coating film are shown in Table 1.

Comparative Example 3

Figure 12:
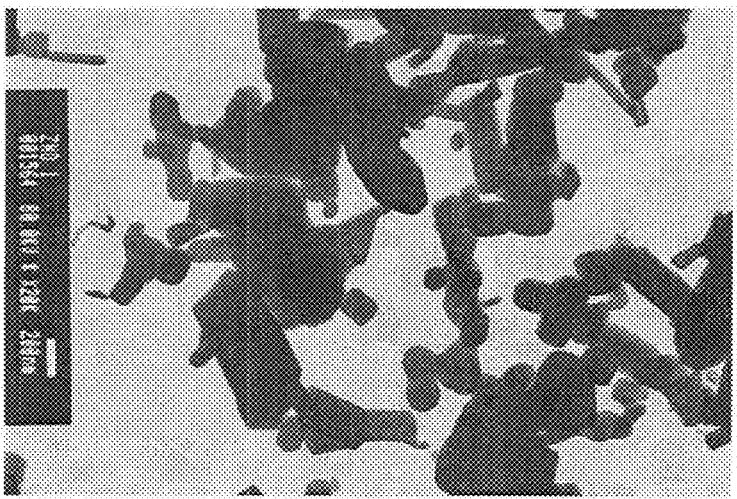
FIG. 12 is a transmission electron microscope photograph of zinc oxide particles (Zinc oxide No. 1 manufactured by Sakai Chemical Industry Co., Ltd.) used in Comparative Example 3.

Zinc oxide No. 1 (manufactured by Sakai Chemical Industry Co., Ltd., particle diameter: 0.31 μm) was evaluated in the same manner as in the examples. The electron microscope photograph is shown in FIG. 12. The results of evaluating the physical properties of the particles are shown in Table 1.

Comparative Example 4

Figure 13:
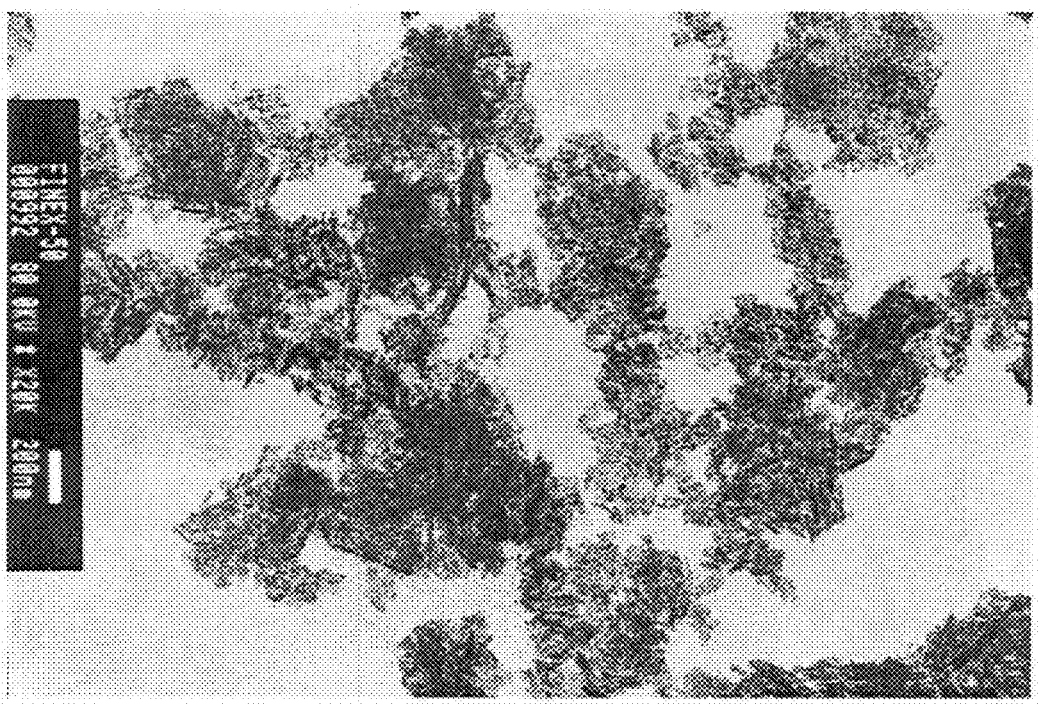
FIG. 13 is a transmission electron microscope photograph of zinc oxide particles (FINEX-50 manufactured by Sakai Chemical Industry Co., Ltd.) used in Comparative Example 4.

FINEX-50 (manufactured by Sakai Chemical Industry Co., Ltd., particle diameter: 0.02 μm) was evaluated in the same manner as in the examples. The electron microscope photograph is shown in FIG. 13. The results of evaluating the physical properties of the particles are shown in Table 1.

Comparative Example 5

Figure 14:
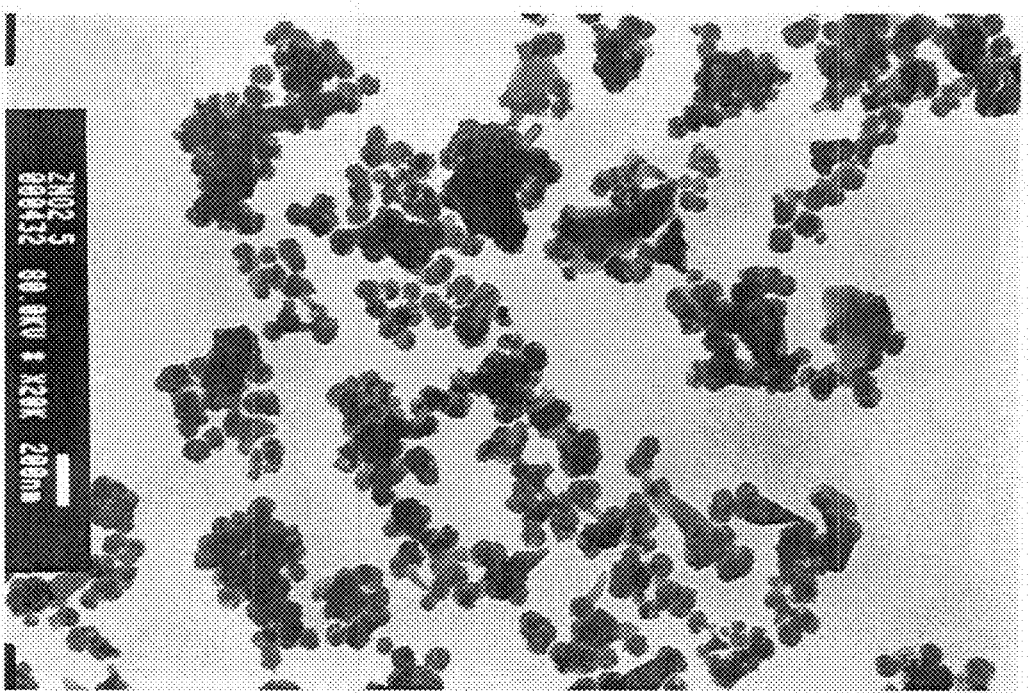
FIG. 14 is a transmission electron microscope photograph of particles obtained in Comparative Example 5.
Figure 15:
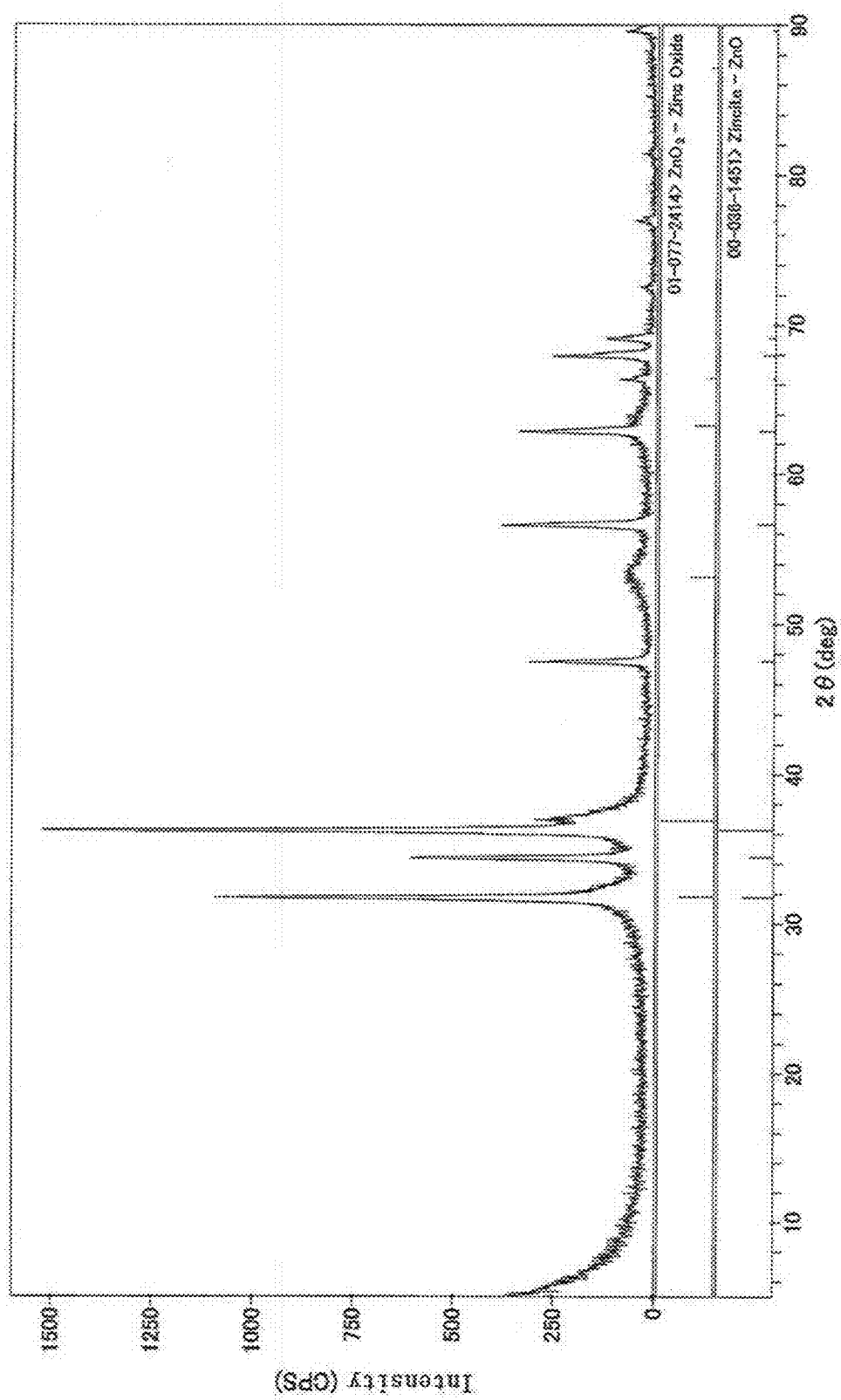
FIG. 15 is an X-ray diffraction spectrum of particles obtained in Comparative Example 5.

In water was repulped 16.28 g of SF-15 (manufactured by Sakai Chemical Industry Co., Ltd., particle diameter: 0.08 μm) to prepare 500 ml of a slurry in a concentration of 0.4 mol/l in terms of zinc oxide. Subsequently, 10.38 g of hydrogen peroxide water (manufactured by Wako Pure Chemical Industries, Ltd.; content of hydrogen peroxide: 30.0 to 35.5% by weight) was added to water to prepare 500 ml an aqueous hydrogen peroxide solution in a concentration of 0.2 mol/l in terms of hydrogen peroxide. Subsequently, 500 ml of the water slurry of SF-15 was stirred, 500 ml of the aqueous hydrogen peroxide solution was added thereto, and the mixture was subjected to a stirring treatment for 6 hours with the treatment temperature set at 25° C. After the stirring treatment, the mixture was filtrated, washed with water, and dried at 110° C. for 12 hours to obtain particles. The size and form of the obtained particles were observed with a transmission electron microscope (TEM, JEM-1200EX II, manufactured by JEOL Ltd.). The obtained electron microscope photograph is shown in FIG. 14. Further, the X-ray diffraction spectrum of the obtained particles is shown in FIG. 15. The results of evaluating the physical properties of the obtained particles are shown in Table 1. It has become apparent from the electron microscope photograph that the obtained particles include rounded particles and indefinite-shaped particles in a mixed state, and it has become apparent from the X-ray diffraction spectrum that the obtained particles are a mixture of zinc oxide and zinc peroxide. From these results, it is considered that in the conditions described above, a reaction of SF-15 as raw material zinc oxide particles with hydrogen peroxide does not sufficiently proceed, and raw material zinc oxide particles remain.

(Average Particle Diameter)

Herein, the average particle diameter is a particle diameter (μm) defined by a unidirectional diameter in a visual field of 2000 to 100000 magnification in a transmission electron microscope (TEM, JEM-1200EX II, manufactured by JEOL Ltd.) photograph (distance between two parallel lines in a fixed direction with a particle held therebetween; measurements are made in a fixed direction regardless of shapes of particles on the image), and is obtained by measuring the unidirectional diameters of 250 particles in the TEM photograph and determining an average value of a cumulative distribution thereof.

(Aspect Ratio)

The aspect ratio is a ratio between the lengths of a major axis and a minor axis passing through the center of the major axis of zinc peroxide particles or zinc oxide particles: major axis/minor axis in a visual field of 2000 to 100000 magnification in a transmission electron microscope (TEM, JEM-1200EX II, manufactured by JEOL Ltd.) photograph, and is obtained by measuring the aspect ratio for 250 particles in TEM photograph and determining an average value of a cumulative distribution thereof.

(D50, D90, D10, D90/D10)

Herein, D50, D90 and D10 of particles are values measured by a laser diffraction/scattering particle size distribution measuring device LA-750 (manufactured by HORIBA, Ltd.). In a mayonnaise bottle having a volume of 75 ml, 0.5 g of the zinc oxide particles in each of examples and comparative examples, 20 ml of an aqueous sodium hexametaphosphate solution in a concentration of 0.025% by weight in terms of sodium hexametaphosphate, and 88 g of zirconia beads of 0.3 mm φ (manufactured by Toray Industries, Inc., crushing balls) were put and sufficiently mixed, the mixture was then fixed in Paint conditioner Model 5410 (manufactured by Red Devil, Inc.), and subjected to a dispersion treatment by giving vibrations for 45 minutes to thereby prepare a slurry, and a measurement was performed using the slurry. The measurement was performed with the relative refractive index set at 1.5. D50 denotes a 50% cumulative particle diameter on the volume basis, D90 denotes a 90% cumulative particle diameter on the volume basis, and D10 denotes a 10% cumulative particle diameter on the volume basis. A ratio of D90/D10 is calculated as an indicator of sharpness of the particle size distribution. The particle size distribution broadens as the value becomes larger, while the particle size distribution sharpens as the value becomes smaller. That is, as the value of D90/D10 becomes smaller, the numbers of particles having an extremely large particle diameter and particles having an extremely small particle diameter decrease, so that particle sizes become more uniform.

(Preparation of Coating Film)

In a mayonnaise bottle having a volume of 75 ml, 2 g of zinc oxide particles in each of examples and comparative examples described above, 10 g of varnish (ACRYDIC A-801-P manufactured by DIC Corporation), 5 g of butyl acetate (special grade reagent, manufactured by Wako Pure Chemical Industries, Ltd.), 5 g of xylene (genuine special grade, manufactured by JUNSEI CHEMICAL CO., LTD.) and 38 g of glass beads (1.5 mm, manufactured by Potters-Ballotini Co., Ltd.) were put and sufficiently mixed, then fixed in a paint conditioner Model 5410 (manufactured by RED DEVIL, Inc.), and subjected to a dispersion treatment by giving vibrations for 90 minutes, thereby preparing a coating. Next, a small amount of the prepared coating was added dropwise onto a slide glass (length/width/thickness=76 mm/26 mm/0.8 to 1.0 mm, manufactured by Matsunami Glass Ind., Ltd.), and a coating film was prepared using a bar coater (No. 579 ROD No. 6, manufactured by YASUDA SEIKI SEISAKUSHO, LTD.). The prepared coating film was dried at 20° C. for 12 hours, and then used for measurement of total light transmittance 1, total light transmittance 2, total light transmittance 3, parallel light transmittance 1 and parallel light transmittance 2.

(Total Light Transmittance 1, Total Light Transmittance 2, Total Light Transmittance 3, Parallel Light Transmittance 1 and Parallel Light Transmittance 2)

Herein, total light transmittance 1 (%), total light transmittance 2 (%), total light transmittance 3 (%), parallel light transmittance 1 (%) and parallel light transmittance 2 (%) are values obtained by measuring the prepared coating film using a spectrophotometer V-570 (manufactured by JASCO Corporation). The value of total light transmittance 1 (%) is a value of total light transmittance at a wavelength of 310 nm, the value of total light transmittance 2 (%) is a value of total light transmittance at a wavelength of 350 nm, the value of total light transmittance 3 (%) is a value of total light transmittance at a wavelength of 375 nm, the value of parallel light transmittance 1 (%) is a value of parallel light transmittance at a wavelength of 500 nm, and the value of parallel light transmittance 2 (%) is a value of parallel light transmittance at a wavelength of 700 nm. An ultraviolet blocking effect to ultraviolet rays having a wavelength of UVB is enhanced as the value of total light transmittance 1 (%) becomes smaller, and an ultraviolet blocking effect to ultraviolet rays having a wavelength of UVA is enhanced as the values of total light transmittance 2 (%) and total light transmittance 3 (%) become smaller. Particularly, when the value of total light transmittance 3 (%) is small, a blocking region to ultraviolet rays having a wavelength of UVA extends over a wider range. Visible light transparency is enhanced as the values of parallel light transmittance 1 (%) and parallel light transmittance 2 (%) become larger.

(X-ray diffraction spectra, Composition of Obtained Particles)

The X-ray diffraction spectra shown in FIGS. 3, 6 and 15 and the compositions of the obtained particles in Table 1 show results of performing analysis using an X-ray diffractometer UltimaIII (manufactured by Rigaku Corporation) having an X-ray tube with copper.

TABLE 1

|  |  | Example 1 | Example 2 | Example 3 | Example 4 | Example 5 | Example 6 |
|---|---|---|---|---|---|---|---|
| Preparation conditions | Raw material zinc oxide particles | SF-15 | SF-15 | Fine zinc oxide | Fine zinc oxide | Zinc oxide No. 1 | FINEX-50 |
|  | Particle diameter of raw material zinc oxide particles (μm) | 0.08 | 0.08 | 0.11 | 0.11 | 0.31 | 0.02 |
|  | Amount of raw material zinc oxide particles (g) | 16.28 | 16.28 | 16.28 | 16.28 | 16.28 | 16.28 |
|  | Concentration of slurry of raw material zinc oxide particles (mol/l) | 0.4 | 0.4 | 0.4 | 0.4 | 0.4 | 0.4 |
|  | Amount of slurry of raw material zinc oxide particles (ml) | 500 | 500 | 500 | 500 | 500 | 500 |
|  | Amount of hydrogen peroxide water (g) | 20.77 | 20.77 | 20.77 | 20.77 | 20.77 | 20.77 |
|  | Concentration of aqueous hydrogen peroxide solution (mol/l) | 0.4 | 0.4 | 0.4 | 0.4 | 0.4 | 0.4 |
|  | Amount of aqueous hydrogen peroxide solution (ml) | 500 | 500 | 500 | 500 | 500 | 500 |
|  | Amount of hydrogen peroxide (mol as $H_2O_2$) with respect to amount of raw material zinc oxide (mol as ZnO) | Equivalent amount | Equivalent amount | Equivalent amount | Equivalent amount | Equivalent amount | Equivalent amount |
|  | Treatment temperature (° C.) | 25 | 25 | 25 | 25 | 25 | 25 |

TABLE 1-continued

|  |  |  |  |  |  |  |  |
|---|---|---|---|---|---|---|---|
|  | Treatment time (Hr) | 6 |  | 6 |  | 6 | 6 |
|  | Calcinating temperature/calcinating time |  | 500° C./ 2 Hr |  | 500° C./ 2 Hr |  |  |
| Physical properties of particles | Composition of obtained particles | Zinc peroxide | Zinc oxide | Zinc peroxide | Zinc oxide | Zinc peroxide | Zinc peroxide |
|  | Shape of obtained particles | Rounded shape | Rounded shape | Rounded shape | Rounded shape | Rounded shape | Rounded shape |
|  | Average particle diameter (μm) | 0.11 | 0.10 | 0.13 | 0.12 | 0.36 | 0.05 |
|  | Aspect ratio | 1.1 | 1.2 | 1.2 | 1.2 | 1.3 | 1.1 |
|  | D50 (μm) |  | 0.13 |  | 0.15 |  |  |
|  | D90 (μm) |  | 0.21 |  | 0.24 |  |  |
|  | D10 (μm) |  | 0.09 |  | 0.09 |  |  |
|  | D90/D10 |  | 2.5 |  | 2.6 |  |  |
|  | Specific surface area (m²/g) |  | 10.3 |  | 7.8 |  |  |
| Physical properties of coating film | Total light transmittance 1 (%) |  | 19 |  | 19 |  |  |
|  | Total light transmittance 2 (%) |  | 17 |  | 17 |  |  |
|  | Total light transmittance 3 (%) |  | 15 |  | 15 |  |  |
|  | Parallel light transmittance 1 (%) |  | 68 |  | 63 |  |  |
|  | Parallel light transmittance 2 (%) |  | 85 |  | 82 |  |  |

|  |  | Comparative Example 1 | Comparative Example 2 | Comparative Example 3 | Comparative Example 4 | Comparative Example 5 |
|---|---|---|---|---|---|---|
| Preparation conditions | Raw material zinc oxide particles | SF-15 | Fine zinc oxide | Zinc oxide No. 1 | FINEX-50 | SF-15 |
|  | Particle diameter of raw material zinc oxide particles (μm) | 0.08 | 0.11 | 0.31 | 0.02 | 0.08 |
|  | Amount of raw material zinc oxide particles (g) |  |  |  |  | 16.28 |
|  | Concentration of slurry of raw material zinc oxide particles (mol/l) |  |  |  |  | 0.4 |
|  | Amount of slurry of raw material zinc oxide particles (ml) |  |  |  |  | 500 |
|  | Amount of hydrogen peroxide water (g) |  |  |  |  | 10.38 |
|  | Concentration of aqueous hydrogen peroxide solution (mol/l) |  |  |  |  | 0.2 |
|  | Amount of aqueous hydrogen peroxide solution (ml) |  |  |  |  | 500 |
|  | Amount of hydrogen peroxide (mol as $H_2O_2$) with respect to amount of raw material zinc oxide (mol as ZnO) |  |  |  |  | 0.5 times |
|  | Treatment temperature (° C.) |  |  |  |  | 25 |
|  | Treatment time (Hr) |  |  |  |  | 6 |
|  | Calcinating temperature/calcinating time |  |  |  |  |  |
| Physical properties of particles | Composition of obtained particles | Zinc oxide | Zinc oxide | Zinc oxide | Zinc oxide | Zinc oxide + zinc peroxide |
|  | Shape of obtained particles | Indefinite shape | Indefinite shape | Indefinite shape | Indefinite shape | Indefinite shape + rounded shape |
|  | Average particle diameter (μm) | 0.09 | 0.11 | 0.33 | 0.02 |  |
|  | Aspect ratio | 2.2 | 2.5 | 2.4 | 1.8 |  |
|  | D50 (μm) | 0.20 | 0.24 | 0.60 | 0.14 |  |
|  | D90 (μm) | 0.50 | 0.58 | 1.13 | 0.25 |  |
|  | D10 (μm) | 0.12 | 0.12 | 0.18 | 0.09 |  |
|  | D90/D10 | 4.2 | 4.6 | 6.1 | 2.9 |  |
|  | Specific surface area (m²/g) | 13.0 | 9.9 | 3.5 | 53.6 |  |
| Physical properties of coating film | Total light transmittance 1 (%) | 25 | 20 | 31 | 15 |  |
|  | Total light transmittance 2 (%) | 24 | 17 | 30 | 16 |  |
|  | Total light transmittance 3 (%) | 24 | 15 | 27 | 54 |  |
|  | Parallel light transmittance 1 (%) | 68 | 53 | 22 | 85 |  |
|  | Parallel light transmittance 2 (%) | 85 | 79 | 48 | 93 |  |

From Table 1, it is evident that the rounded zinc peroxide particles of the present invention are obtained as zinc peroxide particles having a rounded shape even when raw material zinc oxide particles have an indefinite shape. It is evident that the rounded zinc peroxide particles and rounded zinc oxide particles of the present invention have a very small aspect ratio. It has been shown that the rounded zinc oxide particles of examples have a very sharp particle size distribution as compared to the zinc oxide particles of comparative examples. It is also evident that the rounded zinc oxide particles having an average particle diameter of 0.10 μm in Example 2 and the rounded zinc oxide particles having an average particle diameter of 0.12 μm in Example 4 have excellent transparency as compared to the conventional indefinite-shaped zinc oxide particles having an average particle diameter of 0.11 μm in Comparative Example 2. Further, it is evident that the rounded zinc oxide particles of Examples 2 and 4 have low total light transmittance 3 (%), and have excellent ultraviolet blocking performance even in a wavelength range of UVA at 375 nm. On the other hand, the conventional zinc oxide particles of Comparative Examples 1, 3 and 4 had significantly high total light transmittance 3 (%) as compared to those of Examples 2 and 4, so that ultraviolet blocking performance in a wavelength range of UVA at 375 nm could not be sufficiently achieved.

INDUSTRIAL APPLICABILITY

The rounded zinc peroxide particles of the present invention can be used for a cross-linker, a deodorant, a bactericide, a bleaching agent, an oxidant, a photocatalyst and the like.

The rounded zinc oxide particles of the present invention can be used as a component of a cosmetic, a heat releasing filler, a heat releasing resin composition, a heat releasing grease and a heat releasing coating composition.

The invention claimed is:

1. A method for production of rounded zinc oxide particles which have an average particle diameter of 0.1 μm or more and an aspect ratio of 2.0 or less, comprising a step (1) of treating zinc oxide particles with hydrogen peroxide, in which raw material zinc oxide particles are repulped in water to prepare a slurry of raw material zinc oxide particles in a concentration of 10 to 2000 g/l in terms of zinc oxide, an aqueous hydrogen peroxide solution in a concentration of 1 to 500 g/l in terms of hydrogen peroxide is added to the slurry, and the mixture is stirred, and a step (2) of calcinating and thereby thermally decomposing the zinc peroxide obtained in the step (1).

* * * * *